(12) United States Patent
Liu et al.

(10) Patent No.: US 7,501,454 B2
(45) Date of Patent: Mar. 10, 2009

(54) **CYCLOHEXENONE COMPOUNDS FROM *ANTRODIA CAMPHORATA* TO TREAT AUTOIMMUNE DISEASES**

(75) Inventors: Sheng-Yun Liu, Taipei Hsien (TW); Mao-Tien Kuo, Taipei Hsien (TW); Wu-Che Wen, Taipei Hsien (TW)

(73) Assignee: Golden Biotechnology Corporation, Taipei Hsien (TW)

( * ) Notice: Subject to any disclaimer, the term of this patent is extended or adjusted under 35 U.S.C. 154(b) by 128 days.

(21) Appl. No.: 11/882,196

(22) Filed: Jul. 31, 2007

(65) Prior Publication Data

US 2008/0312334 A1  Dec. 18, 2008

(30) Foreign Application Priority Data

Jun. 12, 2007  (TW) .............................. 96121138 A

(51) Int. Cl.
*A61K 31/12* (2006.01)
*C07C 49/543* (2006.01)
(52) U.S. Cl. ...................................... 514/690; 568/377
(58) Field of Classification Search ........................ None
See application file for complete search history.

(56) References Cited

OTHER PUBLICATIONS

New Steroid Acids from *Antrodia cinnamomea*, A fungal Parasite of *Cinnamomum micranthum*, Journal of Natural Products, vol. 58, No. 11, p. 1655, Nov. 1995.
Three new Triterpenoids from *Antrodia cinnamomea*, Journal of Natural Products, vol. 58, No. 3, p. 365, Mar. 1995.
Triterpenoids from *Antrodia cinnamomea*, Phytochemistry, vol. 41, No. 1, pp. 263-267, 1996.
A Sesquiterpene Lactone, Phenyl and Biphenyl compounds from *Antrodia cinnamomea*, Phytochemistry, vol. 39, No. 3, pp. 613-616, 1995.
Steroids and Triterpenoids of *Antodia cinnamomea*—A fungus Parasitic on *Cinnamomum micranthum*, Phytochemistry, vol. 41, No. 5, pp. 1389-1392, 1996.

*Primary Examiner*—Sikarl A Witherspoon
(74) *Attorney, Agent, or Firm*—Rabin & Berdo, P.C.

(57) ABSTRACT

The present invention relates to a compound of Antrodia camphorata used to treat autoimmune diseases, in particular to an extract, 4-hydroxy-2,3-dimethoxy-6-methyl-5(3,7,11-trimethyl-dodeca-2,6,10-trienyl)-cyclohex-2-enone, isolated from Antrodia camphorata, and its use in alleviating symptoms of autoimmune diseases such as systemic lupus erythematosus (SLE). The cyclohexenone compound according to the present invention helps to decrease proteinuria levels and antinuclear antibody titers in SLE mammals in order to alleviate kidney inflammation and disease, as well as the self-damage caused by antinuclear antibodies. The purpose for prevention and treatment of autoimmune diseases and kidney diseases by the natural, side-effect free substance can then be accomplished.

12 Claims, 2 Drawing Sheets
(1 of 2 Drawing Sheet(s) Filed in Color)

A.

B.

C.

CYCLOHEXENONE COMPOUNDS FROM *ANTRODIA CAMPHORATA* TO TREAT AUTOIMMUNE DISEASES

BACKGROUND OF THE INVENTION

1. Field of the Invention

The present invention relates to compounds for the treatment of immune-related diseases, in particular to cyclohexenone compounds isolated and purified from Antrodia camphorata extracts and can be applied in treatment of autoimmune immune diseases such as systemic lupus erythematosus (SLE).

2. The Prior Arts

There are many types of autoimmune diseases result from an aberrant immune response of the body and cause self-destructive. Prominent examples' include systemic lupus erythematosus (SLE), rheumatoid arthritis (RA), Scleroderma, Polymyositis, dermatomyositis, Anaphylactoid purpura, Sjögren's syndrome and the like. Others such as primary biliary cirrhosis (PBC), chronic active hepatitis, and Hashimoto's thyroiditis, are all related to autoimmune diseases. Among them, systemic lupus erythematosus (SLE) is the most serious disease, which is common in women of child-bearing age. SLE patients produce autoantibodies called antinuclear antibodies (ANA) targeted against autoantigens inside cell nucleus. These autoantibodies can cause multiple damages in tissues and organs such as skin, joint, skeleton, kidney, cardiovascular system, agglutination system, intestines and stomach, serous membrane (pericardium, pleura, and peritoneum), neural system and the like. Some of the antibodies form immune complexes when bind with antigens, which can be deposited in cells of different tissues during circulation. Clinical manifestations include butterfly rashes, hemolytic anemia, arthritis, blood vessel inflammation, nephritis and so on. A standard treatment for autoimmune diseases is administration of steroids or other chemical drugs. However, patients on long term treatment exhibited uncomfortable complication or side effects. Therefore, it will be beneficial to the patients if natural and side effect free traditional Chinese herb medicines are used to treat autoimmune diseases.

Antrodia camphorata is also called Chang-Zhi, Niu Chang-Zhi, red camphor mushroom and so on, which is a perennial mushroom belonging to the order Aphyllophorales, the family Polyporaceae. It is an endemic species in Taiwan growing on the inner rotten heart wood wall of Cinnamomum kanehirae Hay. Cinnamoum kanehirai Hay is rarely distributed and being overcut unlawfully, which makes Antrodia camphorata growing inside the tree in the wild became even rare. The price of Antrodia camphorata is very expensive due to the extremely slow growth rate of natural Antrodia camphorata that only grows between June to October.

The fruiting bodies of Antrodia camphorata are perennial, sessile, hard and woody, which exhales strong smell of sassafras (camphor aroma). The appearances are various with plate-like, bell-like, hoof-like, or tower-like shapes. They are reddish in color and flat when young, attached to the surface of wood. Then the brims of the front end become little curled tilted and extend to the surroundings. The color turns to be faded red-brown or cream yellow brown, with ostioles all over. It has very high medical value in this stage.

In traditional Taiwanese medicine, Antrodia camphorata is commonly used as an antidotal, liver protective, anti-cancer drug. Antrodia camphorata, like general edible and medicinal mushrooms, is rich in numerous nutrients including polysaccharides (such as β-glucosan), triterpenoids, superoxide dismutase (SOD), adenosine, proteins (immunoglobulins), vitamins (such as vitamin B, nicotinic acid), trace elements (such as calcium, phosphorus and germanium and so on), nucleic acid, agglutinin, amino acids, steroids, lignins and stabilizers for blood pressure (such as antodia acid) and the like. These physiologically active ingredients are believed to exhibit effects such as: anti-tumor activities, increasing immuno-modulating activities, anti-allergy, anti-bacteria, anti-high blood pressure, decreasing blood sugar, decreasing cholesterol and the like.

Triterpenoids are the most studied component among the numerous compositions of Antrodia camphorata. Triterpenoids are the summary terms for natural compounds, which contain 30 carbon atoms with the pentacyclic or hexacyclic structures. The bitter taste of Antrodia camphorata is from the component of triterpenoids. Three novel ergostane-type triterpenoids (antcin A, antcin B, antcin C) were isolated by Cherng et al. from the fruiting bodies of Antrodia camphorata (Cherng, I. H., and Chiang, H. C. 1995. Three new triterpenoids from Antrodia cinnamomea. J. Nat. Prod. 58: 365-371). Three new compounds zhankuic acid A, zhankuic acid B and zhankuic acid were extracted from the fruiting bodies of Antrodia camphorata with ethanol by Chen et al. (Chen, C. H., and Yang, S. W. 1995. New steroid acids from Antrodia cinnamomea,—a fungus parasitic on Cinnamomum micranthum. J. Nat. Prod. 58: 1655-1661). In addition, Chemg et al. also found three other new triterpenoids from the fruiting bodies of Antrodia camphorata, which are sesquiterpene lactone and 2 biphenyl derived compounds, 4,7-dimethoxy-5-methyl-1,3-benzodioxole and 2,2',5,5'-teramethoxy-3,4,3',4'-bi-methylenedioxy-6,6'-dimethylbiphenyl (Chiang, H. C., Wu, D. P., Cherng, I. W., and Ueng, C. H.1995. A sesquiterpene lactone, phenyl and biphenyl compounds from Antrodia cinnamomea. Phytochemistry. 39: 613-616). In 1996, four novel ergostane-type triterpenoids (antcins E and F and methyl antcinates G and H) were isolated by Chemg et al. with the same analytic methods (Chemg, I. H., Wu, D. P., and Chiang, H. C. 1996. Triteroenoids from Antrodia cinnamomea. Phytochemistry. 41: 263-267). And two ergostane related steroids, zhankuic acids D and E together with three lanosta related triterpenes, 15 alpha-acetyl-dehydrosulphurenic acid, dehydroeburicoic acid, dehydrosulphurenic acid were isolated by Yang et al. (Yang, S. W., Shen, Y. C., and Chen, C. H.1996. Steroids and triterpenoids of Antrodia cinnamomea—a fungus parasitic on Cinnamomum micranthum. Phytochemistry. 41: 1389-1392).

Antrodia camphorata extracts were reported to have the abovementioned effects from the previous experiments, and the components were analyzed in succession. However, the potential use of Antrodia camphorata extracts in treatment of autoimmune diseases has never been reported. Further experiments are needed to identify the effective composition to help treat autoimmune conditions. The natural components of Antrodia camphorata extracts will greatly contributes great beneficial effects in preventing or treating systemic lupus erythematosus if the real effective composition is found. In addition, this will help to prevent the side effects or complication caused by chemical pharmaceutical drugs such as steroids in treating autoimmune disease.

SUMMARY OF THE INVENTION

In order to identify which are the compounds to prevent or treat autoimmune diseases such as SLE from the extracts of Antrodia camphorata, the compound of the formula (1) was isolated and purified in the present invention,

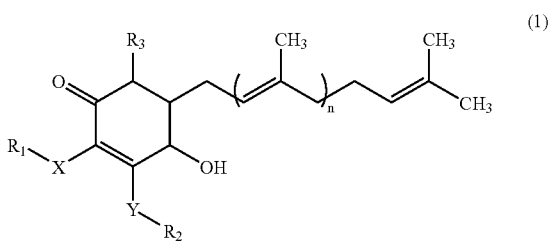

(1)

wherein X and Y can be oxygen or sulfur, $R_1$, $R_2$ and $R_3$ are each a hydrogen atom, methyl, or $(CH_2)_m$—$CH_3$ and m=1-12; n=1-12.

A preferred compound of the general formula (1) is 4-hydroxy-2,3-dimethoxy-6-methyl-5(3,7,11-trimethyl-dodeca-2,6,10-trienyl)-cyclohex-2-enone as shown in formula (2), with molecular formula of $C_{24}H_{38}O_4$, appearance of pale yellow powder and molecular weight of 390.

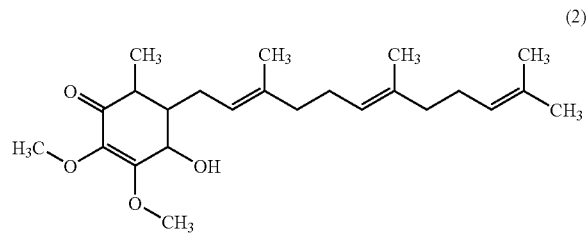

(2)

Cyclohexenone compounds having the structures of formula (1) and formula (2) are purified from aqueous extraction or organic solvent extraction of Antrodia camphorata. The organic solvents used include, but not limited to, alcohols such as methanol, ethanol or propanol, esters such as ethyl acetate, alkanes such as hexane, or halogenated alkanes such as chloromethane, chloroethane. Among them, alcohol is preferred, and ethanol is particularly preferred.

The present invention applies cyclohexenone compounds of the formula (1) and the formula (2) in preventing or treating autoimmune diseases such as SLE. The proteinuria levels in mammals with SLE decreased, which may be due to slow disease progression in nephritis; and the antinuclear antibodies titers in blood also decreased effectively to further alleviate the self-damage caused by antinuclear antibodies when cyclohexenone compounds of Antrodia camphorata was supplemented to mammals with SLE disease. In addition, the natural substance extracted from Antrodia camphorata can be used to alleviate complication and side effects caused by chemical drugs such as steroids and relief the uncomfortable symptoms.

On the other hand, the compounds of formula (1) and/or formula (2) in the present invention can be incorporated into pharmaceutical compositions for treating autoimmune disease such as SLE to improve the symptoms of autoimmune disease in mammals such as human. The pharmaceutical compositions include not only the compounds of formula (1) and/or formula (2), but also the pharmaceutically acceptable carries. Examples of such carriers include, but are not limited to, excipients such as water, fillers such as sucrose or starch, binders such as cellulose derivatives, diluents, disintegrants, absorption enhancers or sweeteners. The pharmaceutical compositions can be manufactured through mixing the compounds of formula (1) and/or formula (2) with at least one of the carriers by means of conventional methods known in the pharmaceutically technical field, which can be formulated, but are not limited to, as powder, tablets, capsules, pellets, granules or other liquid formulation.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

BRIEF DESCRIPTION OF THE DRAWINGS

The patent or application file contains at least one drawing executed in color. Copies of this patent or patent publication with color drawing(s) will be provided by the Office upon request and payment of the necessary fee.

DETAILED DESCRIPTION OF THE PREFERRED EMBODIMENT

Figure 1:
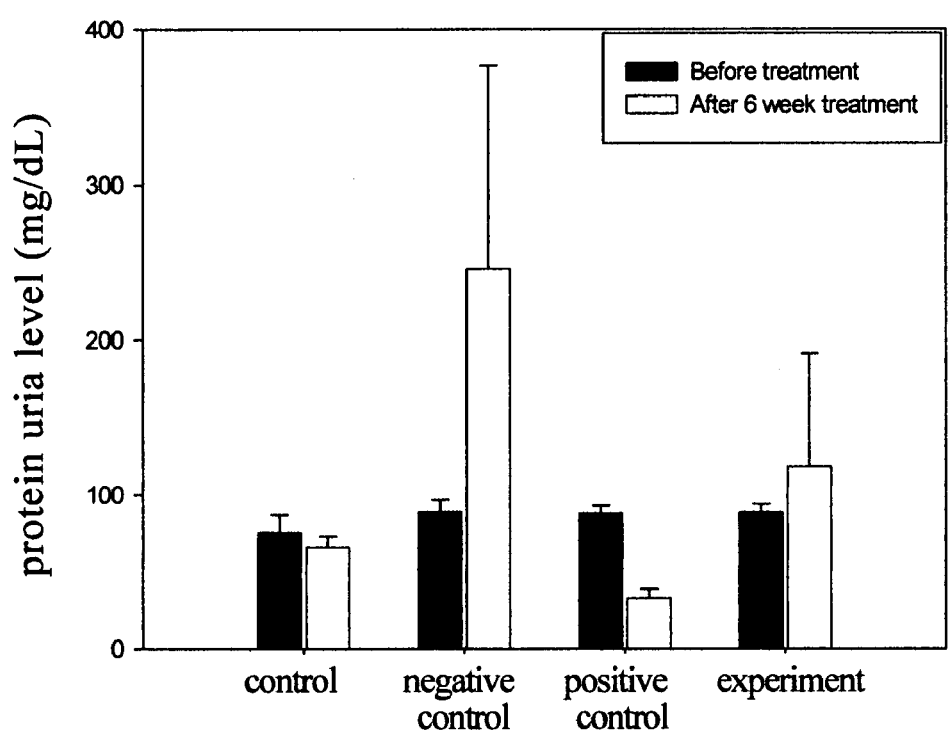
FIG. 1 shows the effects of cyclohexenone compounds from Antrodia camphorata on changes of proteinuria in female NZB/WF1 SLE mice.

The mycelia, fruiting bodies or mixture of both from Antrodia camphorata are first extracted with water or organic solvents to obtain the aqueous extract or organic solvent extract of Antrodia camphorata using the methods well known in the arts. The organic solvents include, but not limited to, alcohols such as methanol; ethanol or propanol; esters such as Ethyl acetate; alkanes such as hexane; or halogenated alkanes such as chloromethane, and chloroethane. Among them, alcohol is preferred, and ethanol is particularly preferred.

The aqueous or organic solvent extracts of Antrodia camphorate were subjected to high-performance liquid chromatography (HPLC) for isolation and purification. Each fraction was recovered and applied to assay for the proteinuria levels, antinuclear antibodies titers and the like after treatment of autoimmune disease such as SLE. The potent fractions with symptom-alleviating function were analyzed for the composition and further assayed with related biochemical tests. The above approach then led to the identification compounds of the formula (1) and/or formula (2) in decreasing levels of urine protein and antinuclear antibodies, and the effects in treating autoimmune disease such as SLE and kidney related disease. In addition, the compounds of the formula (1) and/or formula (2) can be incorporated into the pharmaceutical compositions for treating autoimmune disease such as SLE to let this natural substance effectively improve the symptoms of autoimmune disease without triggering the side effects and complication.

The compound 4-hydroxy-2,3-dimethoxy-6-methyl-5(3,7,11-trimethyl-dodeca-2,6,10-trienyl)-cyclohex-2-enone of the formula (2) are explained below as an example for the present invention. The effects in treatment of autoimmune disease such as SLE was assessed by feeding NZB/WF1 lupus model female mice the abovementioned cyclohexenone compound of Antrodia camphorata and assaying the proteinuria levels and antinuclear antibodies. The above assays have proved that 4-hydroxy-2,3-dimethoxy-6-methyl-5(3,7, 11-trimethyl-dodeca-2,6,10-trienyl)-cyclohex-2-enone from Antrodia camphorata can be used to delay nephritis and kidney damage to decrease the proteinuria level and to effectively inhibit or delay the synthesis of antinuclear antibodies in mammals such as human in order to alleviate the self-damages caused by antinuclear antibodies and further to treat SLE. The details of the examples are described as follows:

Example 1

Isolation of 4-hydroxy-2,3-dimethoxy-6-methyl-5(3,7,11-trimethyl-dodeca-2,6,10-trienyl)-cyclohex-2-enone 100 g of mycelia, fruiting bodies or mixture of both from Antrodia camphorata were placed into a flask. A proper amount of water and alcohol (70-100% alcohol solution) was added into the flask and were stirred at 20-25° C. for at least 1 hour. The solution was filtered through a filter and a 0.45 µm membrane and the filtrate was collected as the extract.

The filtrate of Antrodia camphorata was subjected to High Performance Liquid chromatography (HPLC) analysis. The separation was performed on a RP18 column, the mobile phase consisted of methanol (A) and 0.1-0.5% acetic acid (B), with the gradient conditions of 0-10 min in 95%~20% B, 10-20 min in 20%~10% B, 20-35 min in 10%~10% B, 35-40 min in 10%~95% B, at the flow rate of 1 ml/min. The column effluent was monitored with a UV-visible detector.

The fractions collected at 25-30 min were collected and concentrated to yield 4-hydroxy-2,3-dimethoxy-6-methyl-5 (3,7,11-trimethyl-dodeca-2,6,10-trienyl)-cyclohex-2-enone, a product of pale yellow powder. The analysis of 4-hydroxy-2,3-dimethoxy-6-methyl-5 (3,7,11-trimethyl-dodeca-2,6,10-trienyl)-cyclohex-2-enone showed the molecular formula of $C_{24}H_{38}O_4$, molecular weight of 390, melting point of 48° C.~52° C. Investigation of NMR spectra showed that $^1$H-NMR (CDCl$_3$) δ(ppm)=1.51, 1.67, 1.71, 1.75, 1.94, 2.03, 2.07, 2.22, 2.25, 3.68, 4.05, 5.07, and 5.14; 13C-NMR (CDCl$_3$) δ(ppm)=12.31, 16.1, 16.12, 17.67, 25.67, 26.44, 26.74, 27.00, 39.71, 39.81, 4.027, 43.34, 59.22, 60.59, 120.97, 123.84, 124.30, 131.32, 135.35, 135.92, 138.05, 160.45, and 197.12.

Example 2

Assessment on Effects for Prevention or Treatment of Autoimmune Diseases Such as SLE with Cyclohexenone Compounds of Antrodia Camphorata Autoimmune patients show clinical manifestations of obvious increase in autoantibodies and immune complexes, the antigens of which are normal proteins widely spread in cell nucleus, cytoplasm or cell membrane. The presence of antinuclear antibodies (ANA) is therefore used with diagnostic importance for autoimmune disease screening. Systemic lupus erythematosus (SLE) related antinuclear antibodies target dsDNA (Double-stranded DNA), RNA-related ribonucleoprotein such as Sm, Ro, La, RNP, phospholipids and ribosomal P and so on. Among them, anti-deDNA, anti-Sm and aPL (Antiphospholipid) show the most pathological significance. Anti-dsDNA antibodies are highly specific for SLE and correlate with kidney damage. Therefore, the present invention assesses the effects of cyclohexenone compounds from Antrodia camphorata in SLE prevention or treatment through establishment of an animal model for SLE, detecting the titer of anti-dsDNA antinuclear antibodies in blood and proteinuria level of model animals. The details of the steps are described as follows:

(1) Establishment of an Animal Model for SLE

Female NZB/WF1 mice spontaneously develop human SLE-like syndromes, such as generation of antinuclear autoantibodies, proteinuria, and renal toxicity to cause death. The disease is more severe in female mice than in male mice; the morbidity of female mice is also higher than that of male mice. Therefore, female NZB/WF1 mice were used for screening anti-SLE drugs in this study.

Thirty female NZB/WF1 mice (purchased from Jackson Lab, USA) between 12-24 weeks of age were analyzed biweekly to determine proteinuria levels, monthly to assess the titers of antinuclear autoantibody (ANA). The increased titers of ANA and positive response implicated that female NZB/WF1 mice were going to develop SLE and were ready for grouping. At 22 weeks of age, the animals showing the abovementioned syndromes were randomly divided into 3 groups (10 mice per group, water was administered to negative control group, steroid was given to positive control group, and cyclohexenone compounds of Antrodia camphorata was administered to experiment group), and the start time for the experiment was set as week zero. In addition, ten B6 mice (purchased from National Laboratory Animal Center, Taiwan) without SLE syndrome were normal mice served as blank group. All the groups are treated as shown in Table 1.

TABLE 1

Treatment of animal groups

| | | | Oral administration | |
| Mice strain | group | water | prednisolone 1.25 mg/kg | cyc 50 mg/kg |
| --- | --- | --- | --- | --- |
| B6 | Blank | — | — | — |
| NZB/WF1 female mice (SLE) | Negative control | + | − | − |
| | Positive control | − | + | − |
| | Experiment | − | − | + |

The blank group in Table 1 was B6 mice of no SLE syndrome, which received no treatment and normal diet for natural growth. NZB/WF1 female mice that were able to express SLE syndromes were served in negative control and positive control groups. Mice in the former group received normal water; in the latter were orally medicated with 1.25 mg/kg of prednisolone, the SLE drug. Mice in the experiment group were orally medicated with 50 mg/kg of cyclohexenone compounds from Example 1. The mice were fed with the abovementioned substances once per day starting at 23 weeks of age, and this period of time was referred to as the first week of this experiment. The experiment time consisted of 48 weeks; blood and urine samples were collected routinely to assess the effect of cyclohexenone compounds from Antrodia camphorata to the disease of SLE.

(2) Effects of Cyclohexenone Compounds from Antrodia Camphorata on Changes of Proteinuria in Female NZB/WF1 SLE Mice SLE patients develop renal inflammation and damage, which cause leakage of protein from kidney into the fluid. This leads to increase in proteinuria. The changes of proteinuria can be used to assess the effects of cyclohexenone compounds from Antrodia camphorata on SLE. The urine samples from the mice were collected twice a week. Ten µl of urine was assayed with Bio-Rad Protein Assay Dye Reagent Concentrate (Bio-Rad Laboratories, USA) and read under 450 nm with an ELISA analyzer to determine the protein concentration with a standard curve. The results are shown in FIG. 1.

FIG. 1 shows the changes of proteinuria in female NZB/WF1 SLE mice after use of cyclohexenone compounds from Antrodia camphorata in different groups. The urine protein concentrations of mice in blank group at week 6 were similar to those at week zero (at 28 weeks of age), which were within the normal levels of 65 mg/dl-75 mg/dl. While mice in negative control group showed a 2.76-fold increase in proteinuria levels after 6 weeks of experiment (89.16 mg/dl vs. 246 mg/dl). The typical SLE symptom of a sharp increase in protein excretion due to kidney damage was shown. A low proteinuria level of 32.6 mg/dl was shown in mice given prednisolone from positive control group. The proteinuria level reached 118.2 mg/dl after 6 weeks of experiment for mice oral administrated with 50 mg/kg of cyclohexenone compounds from Antrodia camphorata in the experiment group, which was 1.3-fold increase than that before experiment. Therefore cyclohexenone compounds from Antrodia camphorata could effectively inhibit kidney damage and inflammation caused by SLE, and further alleviated proteinuria symptoms in SLE mice after 6 weeks of feeding. In addition, cyclohexenone of Antrodia camphorata could also be applied in treating excess proteinuria caused by related renal diseases, but is not limited thereto.

(3) Effects of cyclohexenone compounds from Antrodia Camphorata on Changes of Antinuclear Antibodies in Female NZB/WF1 SLE Mice The titers of dsDNA antinuclear antibodies were determined in this study to assess the effects of cyclohexenone compounds from Antrodia camphorata on SLE mice. Blood samples from the mice were collected from the eye sockets every four weeks. Blood cells and plasma were separated after centrifugation. Ten µl of plasma was assayed with Mouse Anti-dsDNA IgG ELISA kit (adi Alpha Diagnostic, USA) to determine the antibody titers. The results are shown in FIG. 2.

Figure 2:
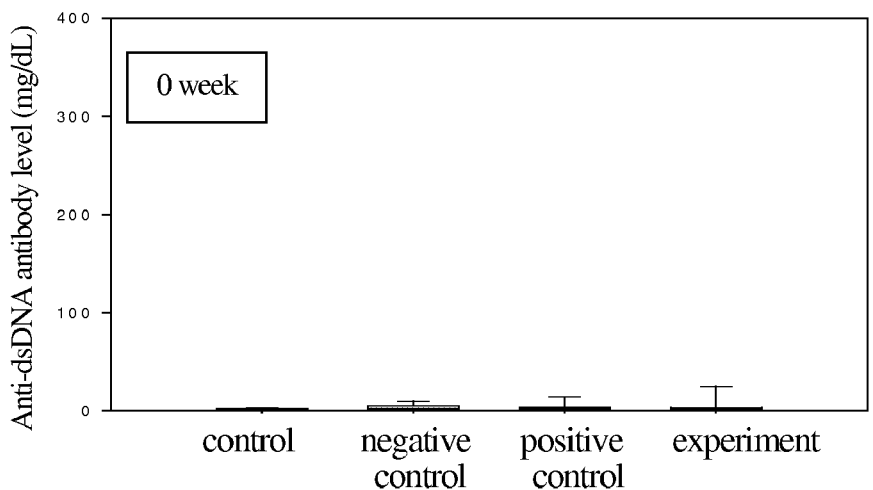
FIG. 2 shows the effects of cyclohexenone compounds from Antrodia camphorata on changes of titers of anti-dsDNA antinuclear antibodies in female NZB/WF1 SLE mice at different time points. Panel (A): week 0; panel (B): week 4; panel (C): week 8.
Figure 2:
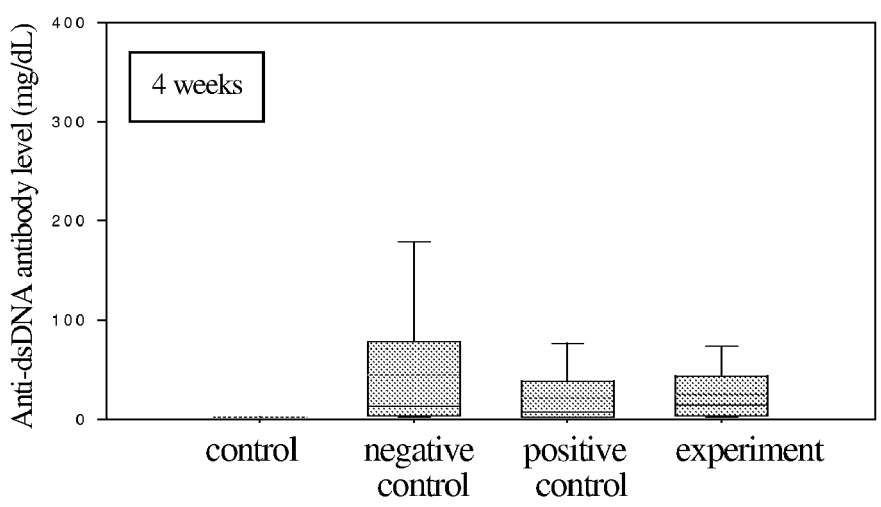
Figure 2:
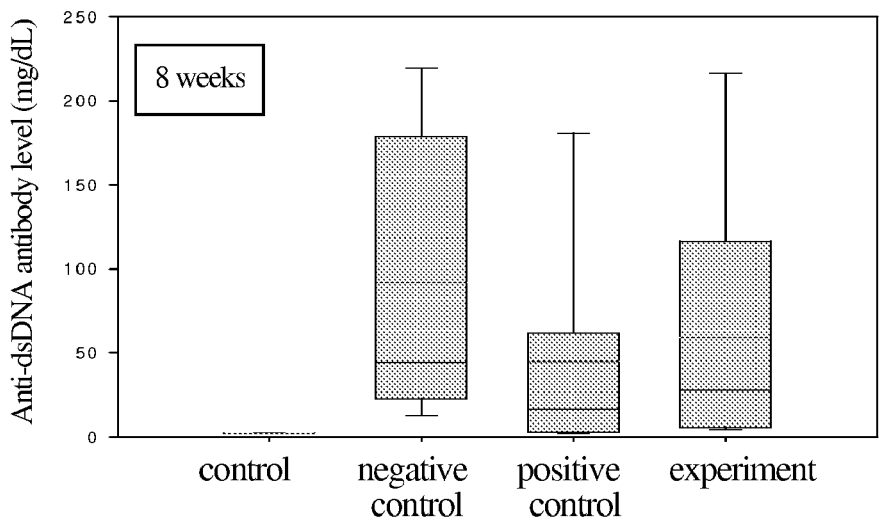

FIG. 2 shows the titers of anti-dsDNA antinuclear antibodies during week 0, week 4 and week 8 in different groups of female NZB/WF1 SLE mice after use of cyclohexenone compounds from Antrodia camphorata. The mice in the blank group having no SLE symptom showed no anti-dsDNA antinuclear antibodies from week 0 to week 8 of experiment (at 22 to 30 weeks of age). While the titers of anti-dsDNA antinuclear antibodies for mice in negative control group were increased from smaller than 10 mg/dl to larger than 150 mg/dl within 8 weeks. The titers of anti-dsDNA antinuclear antibodies for mice in positive group administrated with prednisolone decreased to around 50% at week 8; while mice in the experiment group administrated with cyclohexenone compounds of Antrodia camphorata showed significantly lower titers of anti-dsDNA antinuclear antibodies than those in the negative group during 8 weeks of experiment. The titer of antinuclear antibodies decreased to 34% at week 8 for mice in experiment group. Therefore cyclohexenone compounds from Antrodia camphorata could effectively inhibit or delay the synthesis of antinuclear antibodies in SLE mammals, and further alleviated self damages by antinuclear antibodies in treating SLE disease.

On the other hand, since cyclohexenone compounds from Antrodia camphorata can be used to inhibit or delay the massive synthesis of antinuclear antibodies caused by autoimmune diseases such as SLE, as well as to decrease the proteinuria level due to kidney damage, it can therefore be applied in diseases which will form antinuclear antibodies and cause kidney damages, such as Scleroderma, Sjögren's syndrome, Anaphylactoid purpura, rheumatoid nephritis, or other autoimmune diseases which will cause the damages of tissues and organs including, but not limited to, skin, joint, skeleton, kidney, cardiovascular system, agglutination system, intestines and stomach, serous membrane (pericardium, pleura, peritoneum), neural system. In addition, cyclohexenone compounds from Antrodia camphorata can be used to decrease anti-dsDNA antibodies, further to alleviate the damage to kidney effectively and protect kidney.

In summary, the compound 4-hydroxy-2,3-dimethoxy-6-methyl-5(3,7,11-trimethyl-dodeca-2,6,10-trienyl)-cyclohex-2-enone isolated from Antrodia camphorata according to the invention can be used to effectively treat the symptoms such as high levels of proteinuria and antinuclear antibodies in autoimmune diseases, further to alleviate the self-damages in tissues and organs caused by these diseases in mammals such as human. In addition, the compound can delay the damages to the bodies due to kidney disease based on the protection effects. On the other hand, cyclohexenone compounds from Antrodia camphorata is a natural extract, which won't induce uncomfortable side effects, toxicity or complications. It can be combined with chemical drugs to have lower doses of steroids fewer toxic side effects. In addition, it can be incorporated into pharmaceutical compositions. The pharmaceutical compositions include not only the cyclohexenone compounds from Antrodia camphorata, but also the pharmaceutically acceptable carries. Examples of such carriers include, but are not limited to, excipients such as water, fillers such as sucrose or starch, binders such as cellulose derivatives, diluents, disintegrants, absorption enhancers or sweeteners. The pharmaceutical compositions can be manufactured through mixing cyclohexenone compounds from Antrodia camphorata with at least one of the carriers by means of conventional methods known in the pharmaceutically technical field, which can be formulated in the forms of powder, tablets, capsules, pellets, granules or other liquid formulation, but are not limited to. The purpose for prevention and treatment of autoimmune disease such as SLE and kidney diseases in mammals such as human can then be accomplished.

What is claimed is:

1. A method for the treatment of autoimmune diseases which comprises administering to a subject in need thereof an effective amount of a cyclohexenone compound of Antrodia camphorata having the following formula:

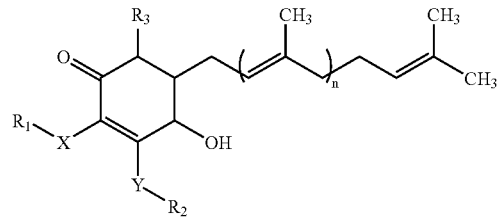

wherein X and Y is oxygen or sulfur, $R_1$, $R_2$ and $R_3$ are each a hydrogen atom, methyl or $(CH_2)_m$—$CH_3$, and m=1-12; n=1-12.

2. The method as claimed in claim 1, wherein the compound is isolated from the organic solvent extracts of Antrodia camphorate.

3. The method as claimed in claim 2, wherein the organic solvents are selected from the group consisting of alcohols, esters, alkanes, and halogenated alkanes.

4. The method as claimed in claim 3, wherein the alcohol is ethanol.

5. The method as claimed in claim 1, wherein the compound is isolated from the aqueous extracts of Antrodia camphorate.

6. The method as claimed in claim 1, wherein the compound is 4-hydroxy-2,3-dimethoxy-6-methyl-5(3,7,11-trimethyl-dodeca-2,6,10-trienyl)-cyclohex-2-enone.

7. The method as claimed in claim 6, wherein the compound can alleviate the kidney damage caused by autoimmune diseases in mammals and the damages in organs and tissues caused by antinuclear antibodies.

8. The method as claimed in claim 7, wherein the mammal is human.

9. The method as claimed in claim 8, wherein the autoimmune disease is systemic lupus erythematosus (SLE).

10. The method as claimed in claim 9, wherein the compound can allievate the kidney damage caused by SLE based on decreasing proteinuria in mammals.

11. The method as claimed in claim 9, wherein the compound can allievate the damages of organ and tissue caused by SLE based on decreasing antinuclear antibodies (ANA) titers in mammals.

12. The method as claimed in claim 11, wherein the antinuclear antibodies are anti-dsDNA antinuclear antibodies.

* * * * *

UNITED STATES PATENT AND TRADEMARK OFFICE
CERTIFICATE OF CORRECTION

PATENT NO. : 7,501,454 B2
APPLICATION NO. : 11/882196
DATED : March 10, 2009
INVENTOR(S) : Sheng-Yun Liu et al.

Page 1 of 1

It is certified that error appears in the above-identified patent and that said Letters Patent is hereby corrected as shown below:

Column 3, Formula (1) should be corrected to:

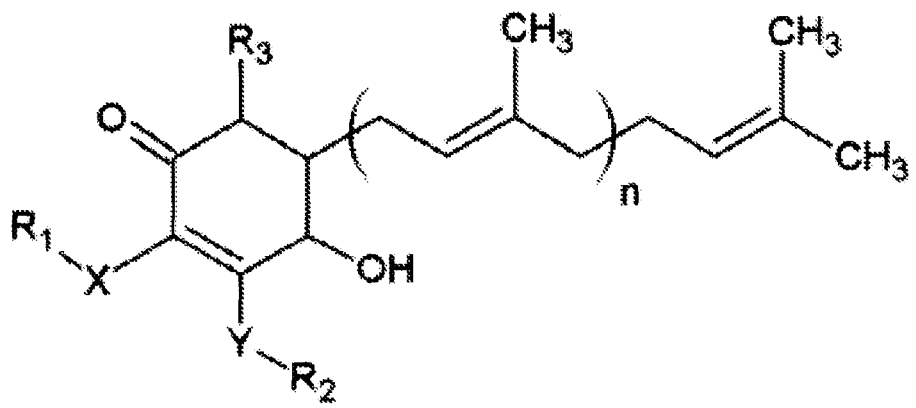

Signed and Sealed this
First Day of February, 2011

David J. Kappos
*Director of the United States Patent and Trademark Office*

UNITED STATES PATENT AND TRADEMARK OFFICE
CERTIFICATE OF CORRECTION

PATENT NO. : 7,501,454 B2  
APPLICATION NO. : 11/882196  
DATED : March 10, 2009  
INVENTOR(S) : Sheng-Yun Liu et al.

It is certified that error appears in the above-identified patent and that said Letters Patent is hereby corrected as shown below:

Column 8, line 45 to 55, Formula should be corrected to:

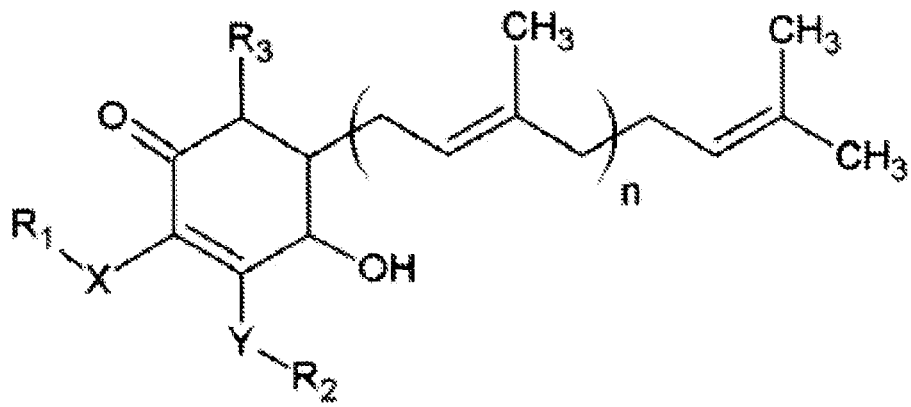

Signed and Sealed this  
Nineteenth Day of April, 2011

David J. Kappos  
*Director of the United States Patent and Trademark Office*